(12) United States Patent
Uchida et al.

(10) Patent No.: US 7,812,175 B2
(45) Date of Patent: Oct. 12, 2010

(54) PROCESS FOR PRODUCTION OF 5-ALKOXY-4-HYDROXYMETHYLPYRAZOLE COMPOUND

(75) Inventors: Yukio Uchida, Shizuoka (JP); Naoya Atsumi, Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 12/223,123

(22) PCT Filed: Feb. 8, 2007

(86) PCT No.: PCT/JP2007/052184

§ 371 (c)(1),
(2), (4) Date: Jul. 23, 2008

(87) PCT Pub. No.: WO2007/094225

PCT Pub. Date: Aug. 23, 2007

(65) Prior Publication Data

US 2009/0036688 A1     Feb. 5, 2009

(30) Foreign Application Priority Data

Feb. 14, 2006   (JP) ............................. 2006-037245

(51) Int. Cl.
  *C07D 231/00*  (2006.01)
(52) U.S. Cl. .................................. 548/370.4
(58) Field of Classification Search ............... 548/370.4
  See application file for complete search history.

(56) References Cited

U.S. PATENT DOCUMENTS

| | | | |
|---|---|---|---|
| 7,241,794 B2 * | 7/2007 | Dunn et al. | 514/407 |
| 2004/0235926 A1 | 11/2004 | Sakya | 514/406 |
| 2005/0215797 A1 | 9/2005 | Nakatani et al. | 548/366.1 |

FOREIGN PATENT DOCUMENTS

| WO | WO 2005/085205 | 9/2005 |
|---|---|---|
| WO | WO 2005/095352 | 10/2005 |
| WO | WO 2006/123088 | 11/2006 |

\* cited by examiner

*Primary Examiner*—Kamal A Saeed
*Assistant Examiner*—Valerie Rodriguez-Garcia
(74) *Attorney, Agent, or Firm*—Bacon & Thomas, PLLC

(57) ABSTRACT

The present invention relates to a process for producing a 5-alkoxy-4-hydroxymethylpyrazole compound represented by the general formula (3)

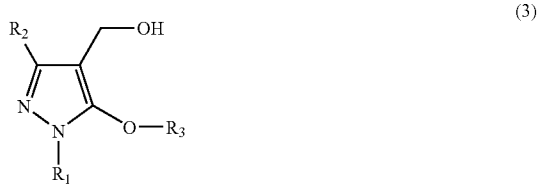

(3)

which comprises reacting a pyrazole compound represented by the general formula (1)

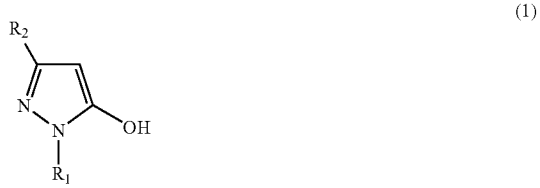

(1)

(wherein $R_1$ is a substituent such as alkyl group, substituted or unsubstituted group or the like, and $R_2$ is an electron withdrawing group) with a compound represented by the general formula (2)

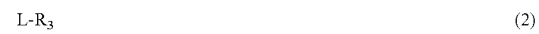

L-$R_3$     (2)

(wherein L is a leaving group and $R_3$ is a substituent such as substituted or unsubstituted alkyl group or the like) in the presence of a base and formaldehyde.

24 Claims, No Drawings

PROCESS FOR PRODUCTION OF 5-ALKOXY-4-HYDROXYMETHYLPYRAZOLE COMPOUND

TECHNICAL FIELD

The present invention relates to a process for producing a 5-alkoxy-4-hydroxymethylpyrazole compound which is useful as an intermediate for production of medicine and agricultural chemical, as well as to a novel 5-alkoxy-4-hydroxymethylpyrazole compound which is produced by the process.

BACKGROUND ART

The 5-alkoxy-4-hydroxymethylpyrazole compound obtained by the present invention is useful as an intermediate for production of medicine and agricultural chemical.

No process is known for production of a 5-alkoxy-4-hydroxymethylpyrazole compound from a 5-hydroxypyrazole compound in a single step.

A process of reducing a 5-alkoxy-4-formylpyrazole is known in order to obtain a 5-alkoxy-4-hydroxymethylpyrazole compound (see Patent Literature 1). In this process, however, since a 5-hydroxypyrazole compound is used as a starting material in order to obtain a 5-alkoxy-4-hydroxymethylpyrazole compound, three-step reactions are required; therefore, in production of an intended product, the operation and work have been complicated, a long time has been needed, and the overall yield of intended product has not been satisfactory.

Patent Literature 1: WO 2004-099157

DISCLOSURE OF THE INVENTION

Task to be Achieved by the Invention

It has been desired to develop a process for producing a 5-alkoxy-4-hydroxymethylpyrazole compound, which is free from the above-mentioned drawbacks of the prior art, is simple in operation and work, and is advantageous in time and yield.

Means for Achieving the Task

In view of the above situation, the present inventor made a concentrated study on the process for production of 5-alkoxy-4-hydroxymethylpyrazole compound. As a result, it was found that a 5-alkoxy-4-hydroxymethylpyrazole compound represented by the general formula (3) shown later is formed by reacting a pyrazole compound represented by the general formula (1) shown later, with a compound represented by the general formula (2) shown later, in the presence of a base and formaldehyde. The finding has led to the completion of the present invention.

Effect of the Invention

The process of the present invention has made it possible to produce a 5-alkoxy-4-hydroxymethylpyrazole compound represented by the general formula (3), in a single step. The present process is simple in operation and work, is advantageous in time and yield of intended product in industrial scale production, and is extremely useful as an industrial process for production of 5-alkoxy-4-hydroxymethylpyrazole compound.

BEST MODE FOR CARRYING OUT THE INVENTION

The present invention is described in detail below.
The present invention has achieved the above-mentioned task by providing the inventions [1] to [21] shown below.

[1] A process for producing a 5-alkoxy-4-hydroxymethylpyrazole compound represented by the general formula (3)

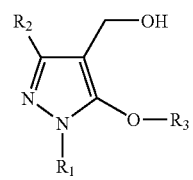

(3)

(wherein $R_1$ is an alkyl group, an aryl group which may have a substituent, or a hetero-aryl group which may have a substituent, $R_2$ is an electron withdrawing group, and $R_3$ is an alkyl group which may have a substituent, a cycloalkyl group which may have a substituent, a cycloalklylalkyl group which may have a substituent, an alkenyl group which may have a substituent, or an alkynyl group which may have a substituent), which comprises reacting a pyrazole compound represented by the general formula (1)

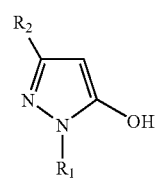

(1)

(wherein $R_1$ and $R_2$ are as defined above) with a compound rep-resented by the general formula (2)

L-$R_3$ (2)

(wherein L is a leaving group and $R_3$ is as defined above) in the presence of a base and formaldehyde.

[2] A process for producing a 5-alkoxy-4-hydroxymethylpyrazole compound according to [1], wherein the leaving group represented by L is a halogen atom, an alkyl-sulfonyloxy group, a haloalkylsulfonyloxy group, or a benzenesulfonyloxy group which may have a substituent.

[3] A process for producing a 5-alkoxy-4-hydroxymethylpyrazole compound according to [1] or [2], wherein the electron withdrawing group represented by $R_2$ is a haloalkyl group, a cyano group or an alkoxycarbonyl group.

[4] A process for producing a 5-alkoxy-4-hydroxymethylpyrazole compound according to [1] or [2], wherein the electron withdrawing group represented by $R_2$ is a (mono- to trifluoro)methyl group.

[5] A process for producing a 5-alkoxy-4-hydroxymethylpyrazole compound according to [1] or [2], wherein the electron withdrawing group represented by $R_2$ is a trifluoromethyl group.

[6] A process for producing a 5-alkoxy-4-hydroxymethylpyrazole compound according to [1] or [2], wherein the electron withdrawing group represented by $R_2$ is a cyano group.

[7] A process for producing a 5-alkoxy-4-hydroxymethylpyrazole compound according to [1] or [2], wherein the electron withdrawing group represented by $R_2$ is a (C1 to C6 alkoxy)carbonyl group.

A process for producing a 5-alkoxy-4-hydroxymethylpyrazole compound according to [1] or [2], wherein the electron withdrawing group represented by $R_2$ is an ethoxycarbonyl group.

[9] A process for producing a 5-alkoxy-4-hydroxymethylpyrazole compound according to any of [1] to [8], wherein the leaving group represented by L is a halogen atom.

[10] A process for producing a 5-alkoxy-4-hydroxymethylpyrazole compound according to any of [1] to [9], wherein the leaving group represented by L is a halogen atom and $R_3$ is a haloalkyl group.

[11] A process for producing a 5-alkoxy-4-hydroxymethylpyrazole compound according to any of [1] to [8], wherein the leaving group represented by L is a chlorine atom and $R_3$ is a difluoromethyl group.

[12] A process for producing a 5-alkoxy-4-hydroxymethylpyrazole compound according to [1], wherein $R_1$ is a methyl group, the electron withdrawing group represented by $R_2$ is a trifluoromethyl group, and the compound represented by the general formula (2) is a chloro(mono- to trihalogen-substituted)methane.

[13] A process for producing a 5-alkoxy-4-hydroxymethylpyrazole compound according to [1], wherein $R_1$ is a methyl group, the electron withdrawing group represented by $R_2$ is a trifluoromethyl group, and the compound represented by the general formula (2) is chlorodifluoromethane.

[14] A 5-alkoxy-4-hydroxymethylpyrazole compound represented by the general formula (4)

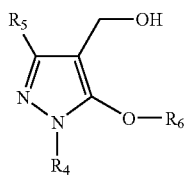

(4)

[wherein $R_4$ is a C1 to C6 alkyl group, an aryl group which may have a substituent or a hetero-aryl group which may have a substituent, $R_5$ is a C1 to C6 haloalkyl group, a cyano group or a (C1 to C6 alkoxy)carbonyl group, and $R_6$ is a C1 to C6 alkyl group which is unsubstituted or substituted with halogen, phenyl group, cyano group or (C1 to C6 alkoxy)carbonyl group, a C3 to C8 cycloalkyl group which is unsubstituted or substituted with halogen, phenyl group, cyano group or (C2 to C6 alkoxy) carbonyl group, a C1 to C6 alkenyl group which is unsubstituted or substituted with halogen, phenyl group, cyano group or (C1 to C6 alkoxy)carbonyl group, or a C2 to C6 alkynyl group which is unsubstituted or substituted with halogen, phenyl group, cyano group or (C1 to C6 alkoxy)carbonyl group].

[15] A 5-alkoxy-4-hydroxymethylpyrazole compound according to [14], wherein $R_5$ is a (mono- to trifluoro)methyl group.

[16] A 5-alkoxy-4-hydroxymethylpyrazole compound according to [14], wherein $R_5$ is a trifluoromethyl group.

[17] A 5-alkoxy-4-hydroxymethylpyrazole compound according to [14], wherein $R_5$ is a cyano group.

[18] A 5-alkoxy-4-hydroxymethylpyrazole compound according to [14], wherein $R_5$ is a (C1 to C6 alkoxy)carbonyl group.

[19] A 5-alkoxy-4-hydroxymethylpyrazole compound according to [14], wherein $R_5$ is an ethoxycarbonyl group.

[20] A 5-alkoxy-4-hydroxymethylpyrazole compound according to [14], wherein $R_4$ is a methyl group, $R_5$ is a trifluoro-methyl group, and $R_6$ is a (mono- to trihalogen-substituted)methyl group.

[21] A 5-alkoxy-4-hydroxymethylpyrazole compound according to [14], wherein $R_4$ is a methyl group, $R_5$ is a trifluoro-methyl group, and $R_6$ is a difluoromethyl group.

The present inventions [1] to [21] are described in de-tail below.

The present invention relates to a process for producing a 5-alkoxy-4-hydroxymethylpyrazole compound represented by the general formula (3), which comprises reacting a pyrazole compound represented by the general formula (1) with a compound represented by the general formula (2) in the presence of a base and formaldehyde, as well as to a novel 5-alkoxy-4-hydroxymethylpyrazole which is produced by the process.

Description is made first on the pyrazole compound represented by the general formula (1), used as a raw material in the present invention.

The pyrazole compound represented by the general formula (1) can be produced based on various processes described in, for example, "Chemistry of Heterocyclic Compounds (written by Hiroshi Yamanaka and others)", Chapter 5, 1988 (Kodansha Scientific); and "Handbook of Heterocyclic Chemistry, 2nd edition (written by J. A. Joule and K. Mills)", Chapter 4.3.2.3, 2000 (Pergamon).

There is known, for example, a process which comprises reacting a corresponding β-ketoester compound with a hydrazine compound. Specifically explaining, it is reported in Journal of Heterocyclic Chemistry, Vol. 27, p. 243 (1990) that, by subjecting ethyl 4,4,4-trifluoroacetoacetate and methylhydrazine to heating and refluxing in a water solvent for 2 hours, 1-methyl-5-hydroxy-3-trifluoromethylpyrazole can be synthesized at a yield of 49%.

Also, there are described, in JP-A-1998-287654, a process which comprises reacting an oxaloacetic acid diester compound with a hydrazine compound to obtain a 3-(alkoxycarbonyl)-5-hydroxypyrazole compound, and a process for converting the alkoxycarbonyl group of the 3-(alkoxycarbonyl)-5-hydroxypyrazole compound obtained by the above process, into cyano group.

Also, there is described, in JP-B-1976-33556, a process which comprises reacting an α-cyanosuccinic acid compound with a diazonium salt compound to obtain a 3-cyano-5-hydroxypyrazole compound.

As the substituent $R_1$ of the general formula (1) representing the pyrazole compound used as a raw material in the present invention, there can be exemplified straight chain or branched chain alkyl groups of 1 to 6 carbon atoms (hereinafter, carbon atoms, in the case of, for ex-ample, 1 to 6 carbon atoms, are abbreviated as C1 to C6), such as methyl group, ethyl group, n-propyl group, isopropyl group, n-butyl group, sec-butyl group, tert-butyl group, n-pentyl group, n-hexyl group and the like;

monocyclic or fused ring aryl groups such as phenyl group, naphthyl group and the like [the aryl groups may each have at least one substituent selected from halogen atoms (e.g. bromo, chloro, fluoro and iodo), straight chain or branched chain C1 to C6 alkyl groups (e.g. methyl group, ethyl group, n-propyl group, isopropyl group, n-butyl group, sec-butyl group, tert-butyl group, n-pentyl group and n-hexyl group), hydroxyl group, straight chain or branched chain C1 to C6 alkoxy groups (e.g. methoxy group, ethoxy group, n-propoxy group and isopropoxy group), straight chain or branched chain C1 to C6 hydroxyalkyl groups (e.g. hydroxymethyl group and 1-hydroxyethyl group), (straight chain or branched chain C1 to C6 alkoxy)-(straight chain or branched chain C1 to C6 alkyl) groups (e.g. methoxymethyl group, 1-methoxyethyl group and 1-ethoxyethyl group), straight chain or branched chain C1 to C6 haloalkyl groups (e.g. fluoromethyl group, difluoromethyl group and trifluoromethyl group), carboxyl group, carboxyl group metal salts typified by alkali metal salts (e.g. sodium salt, potassium salt and lithium salt) or alkaline earth metal salts (e.g. calcium salt, barium salt and magnesium salt), (straight chain or branched chain C1 to C6 alkoxy)carbonyl groups (e.g. methoxycarbonyl group and ethoxycarbonyl group), nitro group, amino group, straight chain or branched chain mono- or di(C1 to C6 alkyl)amino groups (e.g. methylamino group, dimethylamino group, ethylamino group and diethylamino group), (straight chain or branched chain C1 to C6 alkyl)carbonylamino groups (e.g. acetylamino group, propionylamino group and butyrylamino group), straight chain or branched chain hydroxycarbonyl(C1 to C6 alkyl) groups (e.g. hydroxycarbonylmethyl group and 1-hydroxycarbonylethyl group), (straight chain or branched chain C1 to C6 alkoxy)carbonyl-(C1 to C6 alkyl) groups (e.g. methoxycarbonylmethyl group, 1-methoxycarbonylethyl group and 1-ethoxycarbonylethyl group), straight chain or branched chain aminocarbonyl-(C1 to C6 alkyl) groups (e.g. aminocarbonylmethyl group and 1-aminocarbonylethyl group), (straight chain or branched chain C1 to C6 alkyl) aminocarbonyl-(straight chain or branched chain C1 to C6 alkyl) groups (e.g. methylaminocarbonylmethyl group, 1-methylaminocarbonylethyl group and 1-ethylaminocarbonylethyl group), cyano group, etc.]; and monocyclic or fused ring heteroaryl groups having at least one hetero atom selected from nitrogen atom, oxygen atom and sulfur atom, such as pyridyl group, thienyl group, oxazolyl group, thiazolyl group, isoxazolyl group and the like [the heteroaryl groups may each have at least one substituent selected from straight chain or branched chain C1 to C6 alkyl groups (e.g. methyl group, ethyl group, n-propyl group, isopropyl group, n-butyl group, sec-butyl group, tert-butyl group, n-pentyl group and n-hexyl group), hydroxyl group, straight chain or branched chain C1 to C6 alkoxy groups (e.g. methoxy group, ethoxy group, n-propoxy group and isopropoxy group), straight chain or branched chain C1 to C6 hydroxyalkyl groups (e.g. hydroxymethyl group and hydroxyethyl group), (straight chain or branched chain C1 to C6 alkoxy)-(straight chain or branched chain C1 to C6 alkyl groups (e.g. methoxy-methyl group, methoxyethyl group and ethoxyethyl group), straight chain or branched chain C1 to C6 haloalkyl groups (e.g. fluoromethyl group, difluoromethyl group and trifluoro-methyl group), carboxyl group, carboxyl group metal salts typified by alkali metal salts (e.g. sodium salt, potassium salt and lithium salt) or alkaline earth metal salts (e.g. calcium salt, barium salt and magnesium salt), (straight chain or branched chain C1 to C6 alkoxy)carbonyl groups (e.g. methoxycarbonyl group and ethoxycarbonyl group), halogen atoms (e.g. bromo, chloro, fluoro and iodo), nitro group, amino group, straight chain or branched chain mono- or di(C1 to C6 alkyl)amino groups (e.g. methylamino group, dimethylamino group, ethylamino group and diethylamino group), (straight chain or branched chain C1 to C6 alkyl)carbonylamino groups (e.g. acetylamino group, propionylamino group and butyrylamino group), cyano group, formyl group, (straight chain or branched chain C1 to C6 alkyl)carbonyl groups (e.g. methylcarbonyl group and ethylcarbonyl group), arylcarbonyl groups (e.g. benzoyl group and naphthoyl group), etc.]. As the substituent $R_1$, there can further be exemplified aryl groups having at least one substituent selected from (aryl of the above meaning)-carbonyl groups (e.g. benzoyl group and naphthoyl group), (heteroaryl of the above meaning)-carbonyl groups (e.g. pyridylcarbonyl group, thienylcarbonyl group and furylcarbonyl group), etc.; and heteroaryl groups having at least one substituent selected from (heteroaryl of the above meaning)-carbonyl groups (e.g. pyridylcarbonyl group, thienylcarbonyl group and furylcarbonyl group), etc.

The electron withdrawing group represented by $R_2$, of the general formula (1) refers to a group (an atomic group) which withdraws electron from other reactant atom or atomic group based on the inductive effect, or an aryl group substituted with an atomic group which withdraws electron from other reactant atom or atomic group based on the inductive effect. As specific examples of the electron withdrawing group, there can be mentioned straight chain or branched chain C1 to C6 haloalkyl groups such as difluoromethyl group, trifluoromethyl group and the like; carboxyl group; carboxyl group metal salts typified by alkali metal salts such as sodium salt, potassium salt, lithium salt and the like, and by alkaline earth metal salts such as calcium salt, barium salt, magnesium salt and the like; (straight chain or branched chain C1 to C6 alkoxy)carbonyl groups such as methoxycarbonyl group, ethoxycarbonyl group and the like; halogen atoms such as bromo, chloro, fluoro, iodo and the like; nitro group; formyl group; (straight chain or branched chain C1 to C6 alkyl) carbonyl groups such as methylcarbonyl group, ethylcarbonyl group and the like; arylcarbonyl groups such as benzoyl group, naphthoyl group and the like; monocyclic or fused ring heteroarylcarbonyl groups having one to four hetero-atoms selected from nitrogen atom, oxygen atom and sulfur atom, such as pyridylcarbonyl group, thienylcarbonyl group, furylcarbonyl group and the like; aminocarbonyl group; mono- or di(straight chain or branched chain C1 to C6 alkyl)aminocarbonyl groups such as methylaminocarbonyl group and dimethylaminocarbonyl group and the like; and cyano group.

Therefore, as specific examples of the pyrazole compound represented by the general formula (1), there can be mentioned 5-hydroxy-1-methyl-3-trifluoromethylpyrazole, 3-ethoxycarbonyl-5-hydroxy-1-methylpyrazole, 3-chloro-5-hydroxy-1-methylpyrazole, 5-hydroxy-1-methyl-3-nitropyrazole, 5-hydroxy-1-methyl-3-(2-thiophenecarbonyl)pyrazole, 5-hydroxy-1-methyl-3-(3-pyridylcarbonyl)pyrazole, 3-dimethylaminocarbonyl-5-hydroxy-1-methylpyrazole, 3-(4-dimethylaminocarbonyl)-5-hydroxy-1-methylphenylpyrazole, 5-hydroxy-1-n-propyl-3-trifluoromethylpyrazole, 3-cyano-1-n-hexyl-5-hydroxypyrazole, 1-tert-butyl-5-hydroxy-3-trifluoromethylpyrazole, 5-hydroxy-1-phenyl-3-trifluoromethylpyrazole, 3-cyano-5-hydroxy-1-phenylpyrazole, 1-(4-chlorophenyl)-3-ethoxycarbonyl-5-hydroxypyrazole, 3-ethoxycarbonyl-5-hydroxy-1-(2-methylphenyl)pyrazole, 3-ethoxycarbonyl-5-hydroxy-1-(2-methoxymethylphenyl)pyrazole, 1-(4-acetylphenyl)-3-ethoxycarbonyl-5-hydroxypyrazole, 3-ethoxycarbonyl-5-hydroxy-1-(3-nitrophenyl)pyrazole, 5-hydroxy-1-(2-methoxyphenyl)-3-trifluoromethylpyrazole, 5-hydroxy-3-trifluoromethyl-1-(4-trifluoromethylphenyl)pyrazole, 1-(4-ethoxycarbonylphenyl)-5-hydroxy-3-trifluoromethylpyrazole, 1-(4-dimethylaminophenyl)-5-hydroxy-3-trifluoromethylpyrazole, 1-(4-acetylaminophenyl)-5-hydroxy-3-trifluoromethylpyrazole, 1-(4-methoxycarbonylmethylphenyl)-5-hydroxy-3-trifluoromethylpyrazole, 1-(4-dimethylaminocarbonylmethylphenyl)-5-hydroxy-3-trifluoromethylpyrazole, 1-(4-cyanophenyl)-5-hydroxy-3-trifluoromethylpyrazole, 1-(2-naphthyl)-5-hydroxy-3-trifluoromethylpyrazole, 1-(2-benzothiazolyl)-5-hydroxy-3-trifluoromethylpyrazole, 5-hydroxy-1-(2-pyridyl)-3-trifluoromethylpyrazole, and 5-hydroxy-1-(2-pyrimidyl)-3-trifluoromethylpyrazole.

Description is then made on the compound represented by the general formula (2).

As the substituent $R_3$ of the general formula (2), there can be exemplified straight chain or branched chain C1 to C6 alkyl groups such as methyl group, ethyl group, n-propyl group, isopropyl group, n-butyl group, sec-butyl group, isobutyl, tert-butyl group, n-pentyl group, 1-methylbutyl group, 2-methylbutyl group, 3-methylbutyl group, 1-ethylpropyl group, 1,1-dimethylpropyl group, 1,2-dimethylpropyl group, neopentyl group, n-hexyl group, 1-methylpentyl group, 2-methylpentyl group, 1-ethylbutyl group, 2-ethylbutyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1,1,2-trimethylpropyl group, 1,2,2-trimethylpropyl group, 1-ethyl-1-methylpropyl group, 1-ethyl-2-methylpropyl group and the like;

C3 to C8 cycloalkyl groups such as cyclopropyl group, cyclobutyl group, cyclopentyl group, cyclohexyl group, cycloheptyl group, cyclooctyl group and the like; C4 to C8 cycloalkylalkyl groups such as cyclopropylmethyl group, 1-cyclopropylethyl group, 2-cyclopropylethyl group, 1-cyclopropylpropyl group, 2-cyclopropylpropyl group, 3-cyclopropylpropyl group, cyclobutylmethyl group, cyclopentylmethyl group, cyclohexylmethyl group and the like;

straight chain or branched chain C2 to C6 alkenyl groups such as vinyl group, 1-propenyl group, isopropenyl group, 2-propenyl group, 1-butenyl group, 1-methyl-1-propenyl group, 2-butenyl group, 1-methyl-2-propenyl group, 3-butenyl group, 2-methyl-1-propenyl group, 1,3-butadienyl group, 1-pentenyl group, 1-ethyl-2-propenyl group, 2-pentenyl group, 1-methyl-1-butenyl group, 3-pentenyl group, 1-methyl-2-butenyl group, 4-pentenyl group, 1-methyl-3-butenyl group, 3-methyl-1-butenyl group, 1,2-dimethyl-2-propenyl group, 1,1-dimethyl-2-propenyl group, 2-methyl-2-butenyl group, 3-methyl-2-butenyl group, 1,2-dimethyl-1-propenyl group, 2-methyl-3-butenyl group, 3-methyl-3-butenyl group, 1,3-pentadienyl group, 1-vinyl-2-propenyl group, 1-hexenyl group, 1-propyl-2-propenyl group, 2-hexenyl group, 1-methyl-1-pentenyl group, 1-ethyl-2-butenyl group, 3-hexenyl group, 4-hexenyl group, 5-hexenyl group, 1-methyl-4-pentenyl group, 1-ethyl-3-butenyl group, 1-(isobutyl)vinyl group, 1-ethyl-1-methyl-2-propenyl group, 1-ethyl-2-methyl-2-propenyl group, 1-isopropyl-2-propenyl group, 2-methyl-2-pentenyl group, 3-methyl-3-pentenyl group, 4-methyl-3-pentenyl group, 1,3-dimethyl-2-butenyl group, 1,1-dimethyl-2-butenyl group, 3-methyl-4-entenyl group, 4-methyl-4-pentenyl group, 1,2-dimethyl-3-butenyl group, 1,3-dimethyl-3-butenyl group, 1,1,2-trimethyl-2-propenyl group, 1,5-hexadienyl group, 1-vinyl-3-butenyl group, 2,4-hexadienyl group and the like; and straight chain or branched chain C2 to C6 alkynyl groups such as ethynyl group, 1-propynyl group, 2-propynyl group, 1-butynyl group, 1-methyl-2-propynyl group, 2-butynyl group, 3-butynyl group, 1-pentynyl group, 1-ethyl-2-propynyl group, 2-pentynyl group, 3-pentynyl group, 1-methyl-2-butynyl group, 4-pentynyl group, 1-methyl-3-butynyl group, 2-methyl-3-butynyl group, 1-hexynyl group, 1-(n-propyl)-2-propynyl group, 2-hexynyl group, 1-ethyl-2-butynyl group, 3-hexynyl group, 1-methyl-2-pentynyl group, 1-methyl-3-pentylnyl group, 4-methyl-1-pentynyl group, 3-methyl-1-pentynyl group, 5-hexynyl group, 1-ethyl-3-butynyl group, 1-ethyl-1-methyl-2-propynyl group, 1,1-dimethyl-2-butynyl group, 2,2-dimethyl-3-butynyl group and the like.

Each of the above-mentioned straight chain or branched chain C1 to C6 alkyl groups, C3 to C6 cycloalkyl groups, C4 to C8 cycloalkylalkyl groups, straight chain or branched chain C2 to C6 alkenyl groups and straight chain or branched chain C1 to C6 alkynyl groups may have at least one substituent selected from halogen atoms such as bromo, chloro, fluoro, iodo and the like;

straight chain or branched chain C1 to C6 alkoxy groups such as methoxy group, ethoxy group, n-propoxy group, isopropoxy group, butoxy group, pentyloxy group, hexyloxy group and the like;

straight chain or branched chain C1 to C6 hydroxyalkyl groups such as hydroxymethyl group, 1-hydroxyethyl group and the like;

(straight chain or branched chain C1 to C6 alkoxy)-(straight chain or branched chain C1 to C6 alkyl) groups such as methoxymethyl group, ethoxyethyl group, 1-methoxyethyl group, 1-methoxypropyl group, 1-methoxybutyl group, 1-ethoxyethyl group, 1-ethoxypropyl group, 1-ethoxybutyl group, 1-methoxy-2-methylpropyl group and the like;

straight chain or branched chain C1 to C6 haloalkyl groups such as fluoromethyl group, chloromethyl group, bromomethyl group, difluoromethyl group, dichloromethyl group, dibromomethyl group, trifluoromethyl group, trichloromethyl group, chlorodifluoromethyl group, bromodifluoromethyl group, 2-fluoroethyl group, 1-chloroethyl group, 2-chloroethyl group, 1-bromoethyl group, 2-bromoethyl group, 2,2-difluoroethyl group, 1,2-dichloroethyl group, 2,2-dichloroethyl group, 2,2,2-trifluoroethyl group, 2,2,2-trichloroethyl group, 1,1,2,2-tetrafluoroethyl group, pentafluoroethyl group, 2-bromo-2-chloroethyl group, 2-chloro-1,1,2,2-tetrafluoroethyl group, 1-chloro-1,2,2,2-tetrafluoroethyl group, 1-chloropropyl group, 2-chloropropyl group, 3-chloropropyl group, 1-bromopropyl group, 2-bromopropyl group, 3-bromopropyl group, 2-bromo-1-methylethyl group, 3-iodopropyl group, 2,3-dichloropropyl group, 2,3-dibromopropyl group, 3,3,3-trifluoropropyl group, 3,3,3-trichloropropyl group, 3-bromo-3,3-difluoropropyl group, 3,3-dichloro-3-fluoropropyl group, 2,2,3,3-tetrafluoropropyl group, 1-bromo-3,3,3-trifluoropropyl group, 2,2,3,3,3-pentafluoropropyl group, 2,2,2-trifluoro-1-trifluoromethylethyl group, heptafluoropropyl group, 1,2,2,2-tetrafluoro-1-trifluoromethylethyl group, 2,3,-dichloro-1,1,2,3,3-pentafluoropropyl group, 2-chlorobutyl group, 3-chlorobutyl group, 4-chlorobutyl group, 2-chloro-1,1-dimethylethyl group, 4-bromobutyl group, 3-bromo-2-methylpropyl group, 2-bromo-1,1-dimethylethyl group, 2,2-dichloro-1,1-dimethylethyl group, 2-chloro-1-chloromethyl-2-methylethyl group, 4,4,4-trifluorobutyl group, 3,3,3-trifluoro-1-methylpropyl group, 3,3,3-trifluoro-2-methylpropyl group, 2,3,4-trichlorobutyl group, 2,2,2-trichloro-1,1-dimethylethyl group, 4-chloro-4,4-difluorobutyl group, 4,4-dichloro-4-fluorobutyl group, 4-bromo-4,4-difluorobutyl group, 2,4-dibromo-4,4-difluorobutyl group, 3,4-dichloro-3,4,4-trifluorobutyl group, 3,3-dichloro-4,4,4-trifluorobutyl group, 4-bromo-3,3,4,4-tetrafluorobutyl group, 4-bromo-3-chloro-3,4,4-trifluorobutyl group, 2,2,3,3,4,4-hexafluorobutyl group, 2,2,3,4,4,4-hexafluorobutyl group, 2,2,2-trifluoro-1-methyl-1-trifluoromethylethyl group, 3,3,3-trifluoro-2-trifluoromethylpropyl group, 2,2,3,3,4,4,4-heptafluorobutyl group, 2,3,3,3-tetrafluoro-2-trifluoromethylpropyl group, 1,1,2,2,3,3,4,4-octafluorobutyl group, nonafluorobutyl group, 4-chloro-1,1,2,2,3,3,4,4-octafluorobutyl group, 5-fluoropentyl group, 5-chloropentyl group, 5,5-difluoropentyl group, 5,5-dichloropentyl group, 5,5,5-trifluoropentyl group, 6,6,6-trifluorohexyl group, 5,5,5,6,6,6-hexafluorohexyl group and the like;

carboxyl group;

carboxyl group metal salts typified by alkali metal salts such as sodium salt, potassium salt, lithium salt and the like, or by alkaline earth metal salts such as calcium salt, barium salt, magnesium salt and the like;

(straight chain or branched chain C1 to C6 alkoxy)carbonyl groups such as methoxycarbonyl group, ethoxycarbonyl group, n-propoxycarbonyl group, isopropoxycarbonyl group, tert-butoxycarbonyl group and the like;

(straight chain or branched chain C1 to C6 alkyl)carbonyl groups such as methylcarbonyl group, ethylcarbonyl group, n-propylcarbonyl group, isopropylcarbonyl group, tert-butylcarbonyl group and the like;

mono-cyclic or fused ring aryl groups which may have a substituent, such as phenyl group, naphthyl group and the like;

mono-cyclic or fused ring heteroaryl groups which may have a substituent, having one to four hetero atoms selected from nitrogen atom, oxygen atom and sulfur atom, typified by pyridyl group, thienyl group, oxazolyl group, thiazolyl group, isoxazolyl group, etc.;

arylcarbonyl groups such as benzoyl group, naphthoyl group and the like;

mono-cyclic or fused ring heteroarylcarbonyl groups having one to four hetero atoms selected from nitrogen atom, oxygen atom and sulfur atom, such as pyridylcarbonyl group, thienylcarbonyl group, furylcarbonyl group and the like;

and so forth.

The L of the general formula (2) is a leaving group, and may be any atom or atomic group as long as it functions as a leaving group in the present reaction. As specific examples thereof, there can be mentioned halogen atoms such as chloro, bromo, iodo and the like; alkylsulfonyloxy groups such as methanesulfonyloxy group, ethanesulfonyloxy group and the like;

haloalkylsulfonyloxy groups such as difluoromethanesulfonyloxy group, trifluoromethanesulfonyloxy group and the like; and benzenesulfonyloxy groups which may have, as a substituent, halogen atom or alkyl group, such as benzenesulfonyloxy group, 4-chlorobenzenesulfonyloxy group, 4-methylbenzenesulfonyloxy group and the like.

Therefore, as specific examples of the compound represented by the general formula (2), there can be mentioned methyl chloride, methyl bromide, methyl iodide, dimethyl sulfate, ethyl bromide, ethyl iodide, diethyl sulfate, n-propyl iodide, isopropyl bromide, n-butyl bromide, sec-butyl iodide, isobutyl iodide, tert-butyl iodide, 1-methylbutyl bromide, 2-methylbutyl iodide, 1-ethylpropyl bromide, 1,1-dimethylpropyl bromide, n-hexyl iodide, 1-methylpentyl iodide, 2-ethylbutyl iodide, 1,1-dimethylbutyl iodide, 1,2-dimethylbutyl iodide, 1,3-dimethylbutyl iodide, 3,3-dimethylbutyl iodide, 1,1,2-trimethylpropyl iodide, cyclopropylmethyl iodide, 2-cyclopropylpropyl iodide, cyclopentylmethyl bromide, cyclo-propyl bromide, cyclopentyl bromide, cyclohexyl bromide, vinyl bromide, isopropenyl bromide, 1-methyl-1-propenyl bromide, 1-methyl-3-butenyl bromide, 1-hexenyl iodide, 1-ethyl-3-butenyl bromide, 1,1,2-trimethyl-2-propenyl bromide, ethynyl bromide, propargyl bromide, 4-pentynyl iodide, 2-hexynyl iodide, 1-ethyl-2-butenyl bromide, 2-bromoethanol, 4-bromo-n-butanol, 1-bromo-2-butanol, chlorofluoromethane, chlorodifluoromethane, 2,2,2-trifluorobromoethane, 1,1,2,2-tetrafluorobromoethane, 3,3,3-trifluoropropyl iodide, 3,3,3-trifluoropropyl bromide, 1,1,2,2,3,3,4,4-nonafluorobutyl bromide, 5,5,6,6,6-pentafluorohexyl bromide, methoxymethyl bromide, ethoxymethyl bromide, isopropoxymethyl iodide, chloroacetic acid, bromoacetic acid, ethyl bromoacetate, n-propyl bromoacetate, isobutyl bromoacetate, bromoacetone, iodoacetone, α-chloroacetophenone, benzyl bromide, 2-bromomethylnaphthalene, 2-chloromethylpyridine, 2-bromomethylfuran, p-toluenesulfonyl-methylpyran and 2-bromomethylthiophene.

Next, description is made on the process for production of 5-alkoxy-4-hydroxymethylpyrazole compound represented by the general formula (3), which comprises reacting the pyrazole compound represented by the general formula (1) with the compound represented by the general formula (2).

The formaldehyde used in the reaction may be in any form. However, it is preferred for simple operation to use a 35 to 50% aqueous formaldehyde solution typified by 35% formalin (which is easily available as a commercial product), or to use paraformaldehyde (this is a formaldehyde polymer and, when hydrolyzed, generates formaldehyde in the reaction system; therefore, this can be used as an equivalent of formaldehyde).

The use amount of formaldehyde may be an amount at least equivalent to the pyrazole compound represented by the general formula (1). However, it may be ordinarily 1.0 to 5.0 equivalents, preferably 1.0 to 3.0 equivalents relative to 1 mole of the pyrazole compound represented by the general formula (1).

The use amount of the compound represented by the general formula (2) may be an amount at least equivalent to the pyrazole compound represented by the general formula (1). However, it may be ordinarily 1.0 to 10.0 equivalents, preferably 1.0 to 3.0 equivalents relative to 1 mole of the pyrazole compound represented by the general formula (1).

As the base used in the present invention, there can be mentioned inorganic bases typified by alkali metal hydrides (e.g. sodium hydride, potassium hydride and lithium hydride), alkali metals (e.g. metallic sodium, metallic potassium and metallic lithium), alkali metal hydroxides (e.g. sodium hydroxide, potassium hydroxide and lithium hydroxide), alkaline earth metal hydroxides (e.g. barium hydroxide, magnesium hydroxide and calcium hydroxide), alkali metal carbonates (e.g. sodium carbonate, potassium carbonate, sodium hydrogencarbonate and potassium hydrogencarbonate), alkaline earth metal oxides (e.g. barium oxide, magnesium oxide and calcium oxide), etc.; and organic bases typified by metal alkoxides (e.g. sodium methoxide, sodium ethoxide, potassium methoxide, potassium ethoxide and potassium tert-butoxide), and alkyl metal such as n-butyl lithium etc. However, an alkali metal hydroxide or an alkali metal carbonate is preferred, and sodium hydroxide, potassium hydroxide or potassium carbonate is particularly preferred.

The use amount of the base may be any amount as long as it allows for sufficient progress of the present reaction. However, the amount is, for example, 1.0 to 20 moles, preferably 3.0 to 10 moles relative to 1 mole of the pyrazole compound (raw material compound) represented by the general formula (1).

The solvent used in the present reaction may be any solvent as long as it does not hinder the reaction. There can be mentioned, for example, water; alcohols such as methanol, ethanol and the like; aromatic hydrocarbons such as toluene, xylene, chlorobenzene and the like; halogenated aliphatic hydrocarbons such as dichloromethane, chloroform and the like; aprotic polar solvents such as dimethylformamide (DMF), dimethylacetamide, N-methylpyrrolidone, tetramethylurea, hexamethylphosphorictriamide (HMPA), propylene carbonate and the like; ether type solvents such as diethyl ether, tetrahydrofuran, dioxane and the like; and aliphatic hydro-carbons such as pentane, n-hexane and the like. Water, an alcohol or an aprotic polar solvent is preferred from the standpoints of solubility for base and reactivity, and water or dimethylformamide (DMF) is particularly preferred. The solvents may be used singly or as a mixed solvent of any mixing ratio.

The use amount of the solvent may be any amount as long as it allows for sufficient stirring of the reaction system. However, it is ordinarily 0.05 to 10 liters, preferably 0.5 to 2 liters relative to 1 mole of the pyrazole compound (raw material compound) represented by the general formula (1).

The temperature of the reaction can be, for example, 0° C. to the refluxing temperature of the solvent used. However, the reaction is preferably conducted at 20 to 50° C., and stirring at room temperature is particularly preferred because it is easy and provides a good yield.

As to the time of the reaction, there is no particular restriction. However, the reaction is complete ordinarily in 1 to 24 hours.

In the present reaction, a 5-alkoxy-4-hydroxymethylpyrazole compound represented by the general formula (3) can be produced in a good yield with a simple operation and under mild conditions. The obtained 5-alkoxy-4-hydroxymethylpyrazole compound represented by the general formula (3) is useful as an intermediate for medicine, agricultural chemical, etc.

Successively, description is made on the present compound of [14] to [21].

The compound of the present invention is represented by the general formula (4)

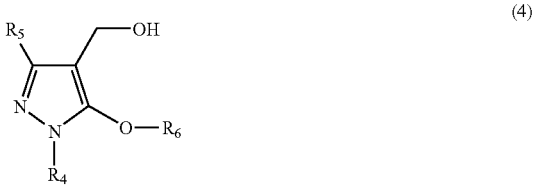

(4)

[wherein $R_4$ is a C1 to C6 alkyl group, an aryl group which may have a substituent or a hetero-aryl group which may have a substituent, $R_5$ is a C1 to C6 haloalkyl group, a cyano group or a (C1 to C6 alkoxy)carbonyl group, and $R_6$ is a C1 to C6 alkyl group which is unsubstituted or substituted with halogen, phenyl group, cyano group or (C1 to C6 alkoxy)carbonyl group, a C3 to C8 cycloalkyl group which is unsubstituted or substituted with halogen, phenyl group, cyano group or (C1 to C6 alkoxy)carbonyl group, a C2 to C6 alkenyl group which is unsubstituted or substituted with halogen, phenyl group, cyano group or (C1 to C6 alkoxy)carbonyl group, or a C2 to C6 alkynyl group which is unsubstituted or substituted with halogen, phenyl group, cyano group or (C1 to C6 alkoxy)carbonyl group].

As the substituent $R_4$ of the general formula (4), there can be exemplified straight chain or branched chain C1 to C6 alkyl groups such as methyl group, ethyl group, n-propyl group, isopropyl group and the like;

aryl groups which may have a substituent, having the same meaning as in the substituent $R_1$; and hetero-aryl groups which may have a substituent, having the same meaning as in the substituent $R_1$.

The $R_5$ of the general formula (4) specifically includes straight chain or branched chain C1 to C6 haloalkyl groups typified by straight chain or branched chain C1 to C6 fluoroalkyl groups such as difluoromethyl group, trifluoromethyl group, 1,2-difluoroethyl group, 2,2-difluoroethyl group, 2,2,2-trifluoroethyl group, 1,1,2,2-tetrafluoroethyl group, pentafluoroethyl group, 3,3,3-trifluoropropyl group, 2,2,3,3-tetrafluoropropyl group, 1,1,3,3,3-pentafluoropropyl group, 2,2,2-trifluoro-1-trifluoromethylethyl group, heptafluoropropyl group and the like;

cyano group; and (straight chain or branched chain C1 to C6 alkoxy)carbonyl groups such as methoxycarbonyl group, ethoxycarbonyl group, n-propoxycarbonyl group, isopropoxycarbonyl group, n-butoxycarbonyl group, 2-butoxycarbonyl group, isobutoxycarbonyl group, n-pentyloxycarbonyl group, neopentyloxycarbonyl group, n-hexyloxycarbonyl group, 2-methylpentyloxycarbonyl group, 2-ethylbutoxycarbonyl group and the like.

As the $R_6$ substituent, there can be exemplified straight chain or branched chain C1 to C6 alkyl groups such as methyl group, ethyl group, n-propyl group, isopropyl group, n-butyl group, sec-butyl group, isobutyl group, tert-butyl group, n-pentyl group, 1-methylbutyl group, 2-methylbutyl group, 3-methylbutyl group, 1-ethylpropyl group, 1,1-dimethylpropyl group, 1,2-dimethylpropyl group, neopentyl group, n-hexyl group, 1-methylpentyl group, 2-methylpentyl group, 1-ethylbutyl group, 2-ethylbutyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1,1,2-trimethylpropyl group, 1,2,2-trimethylpropyl group, 1-ethyl-1-methylpropyl group, 1-ethyl-2-methylpropyl group and the like;

C3 to C8 cycloalkyl groups such as cyclopropyl group, cyclobutyl group, cyclopentyl group, cyclohexyl group, cycloheptyl group, cyclooctyl group and the like;

straight chain or branched chain C2 to C6 alkenyl groups such as vinyl group, 1-propenyl group, isopropenyl group, 2-propenyl group, 1-butenyl group, 1-methyl-1-propenyl group, 2-butenyl group, 1-methyl-2-propenyl group, 3-butenyl group, 2-methyl-1-propenyl group, 1,3-butadienyl group, 1-pentenyl group, 1-ethyl-2-propenyl group, 2-pentenyl group, 1-methyl-1-butenyl group, 3-pentenyl group, 1-methyl-2-butenyl group, 4-pentenyl group, 1-methyl-3-butenyl group, 3-methyl-1-butenyl group, 1,2-dimethyl-2-propenyl group, 1,1-dimethyl-2-propenyl group, 2-methyl-2-butenyl group, 3-methyl-2-butenyl group, 1,2-dimethyl-1-propenyl group, 2-methyl-3-butenyl group, 3-methyl-3-butenyl group, 1,3-pentadienyl group, 1-vinyl-2-propenyl group, 1-hexenyl group, 1-propyl-2-propenyl group, 2-hexenyl group, 1-methyl-1-pentenyl group, 1-ethyl-2-butenyl group, 3-hexenyl group, 4-hexenyl group, 5-hexenyl group, 1-methyl-4-pentenyl group, 1-ethyl-3-butenyl group, 1-(isobutyl)vinyl group, 1-ethyl-1-methyl-2-propenyl group, 1-ethyl-2-methyl-2-propenyl group, 1-isopropyl-2-propenyl group, 2-methyl-2-pentenyl group, 3-methyl-3-pentenyl group, 4-methyl-3-pentenyl group, 1,3-dimethyl-2-butenyl group, 1,1-dimethyl-2-butenyl group, 3-methyl-4-pentenyl group, 4-methyl-4-pentenyl group, 1,2-dimethyl-3-butenyl group, 1,3-dimethyl-3-butenyl group, 1,1,2-trimethyl-2-propenyl group, 1,5-hexadienyl group, 1-vinyl-3-butenyl group, 2,4-hexadienyl group and the like; and straight chain or branched chain C2 to C6 alkynyl groups such as ethynyl group, 1-propynyl group, 2-propynyl group, 1-butynyl group, 1-methyl-2-propynyl group, 2-butynyl group, 3-butynyl group, 1-pentynyl group, 1-ethyl-2-propynyl group, 2-pentynyl group, 3-pentynyl group, 1-methyl-2-butynyl group, 4-pentynyl group, 1-methyl-3-butynyl group, 2-methyl-3-butynyl group, 1-hexynyl group, 1-(n-propyl)-2-propynyl group, 2-hexynyl group, 1-ethyl-2-butynyl group, 3-hexynyl group, 1-methyl-2-pentynyl group, 1-methyl-3-pentynyl group, 4-methyl-1-pentynyl group, 3-methyl-1-pentynyl group, 5-hexynyl group, 1-ethyl-3-butynyl group, 1-ethyl-1-methyl-2-propynyl group, 1,1-dimethyl-2-butynyl group, 2,2-dimethyl-3-butynyl group and the like.

Each of the straight chain or branched chain C1 to C6 alkyl groups, C3 to C8 cycloalkyl groups, straight chain or branched chain C2 to C6 alkenyl groups and straight chain or branched chain C2 to C6 alkynyl groups, represented by $R_6$ may have at least one substituent selected from halogen atoms (e.g. bromo, chloro, fluoro and iodo), phenyl group, cyano group, and (straight chain or branched chain C1 to C6 alkoxy) carbonyl groups (e.g. methoxycarbonyl group, ethoxycarbonyl group, n-propoxycarbonyl group, isopropoxycarbonyl group, n-butoxycarbonyl group, 2-butoxycarbonyl group, isobutoxycarbonyl group, n-pentyloxycarbonyl group, neopentyloxycarbonyl group, n-hexyloxycarbonyl group, 2-methylpentyloxycarbonyl group and 2-ethylbutoxycarbonyl group).

Representative examples of the 5-alkoxy-4-hydroxymethylpyrazole compound represented by the general formula (4), of the present invention are shown in Table 1 and Table 2. However, the 5-alkoxy-4-hydroxymethylpyrazole compound represented by the general formula (4), of the pre-sent invention is not restricted to these examples. The No. of each compound is referred to in later descriptions.

Incidentally, the abbreviations used in Table 1 and Table 2 have the following meanings.

Me: methyl group
Et: ethyl group
n-Pr: n-propyl group
iPr: iso-propyl group
s-Bu: sec-butyl group
n-Pen: n-pentyl group
c-Pen: cyclopentyl group
n-Hex: n-hexyl group
Ph: phenyl group

TABLE 1

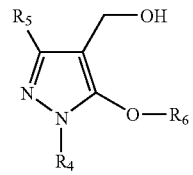

(4)

| Compound No. | $R_4$ | $R_5$ | $R_6$ |
|---|---|---|---|
| 1 | Me | $CH_2F$ | Me |
| 2 | Me | $CH_2F$ | Et |
| 3 | Me | $CH_2F$ | i-Pr |
| 4 | Me | $CHF_2$ | s-Bu |
| 5 | Me | $CHF_2$ | c-Pen |
| 6 | Me | $CHF_2$ | n-Hex |
| 7 | Me | $CF_3$ | Me |
| 8 | Me | $CF_3$ | Et |
| 9 | Me | $CF_3$ | i-Pr |
| 10 | Me | $CF_3$ | s-Bu |
| 11 | Me | $CF_3$ | c-Pen |
| 12 | Me | $CF_3$ | n-Hex |
| 13 | Me | $CF_3$ | $CH_2Ph$ |
| 14 | Me | $CF_3$ | $CH_2CN$ |
| 15 | Me | $CF_3$ | $CH_2COOEt$ |
| 16 | Me | $CF_3$ | $CHF_2$ |
| 17 | Me | $CF_3$ | $CH=CH_2$ |
| 18 | Me | $CF_3$ | $CH=CHCH_2CF_3$ |
| 19 | Me | $CF_3$ | $CH_2CH=C(CH_3)_2$ |
| 20 | Me | $CF_3$ | $CH_2C\equiv CH$ |

TABLE 2

| Compound No. | $R_4$ | $R_5$ | $R_6$ |
|---|---|---|---|
| 21 | Me | $CF_3$ | $CH_2C=CCH_2CF_3$ |
| 22 | Me | $CHFCF_3$ | s-Bu |
| 23 | Me | $CF_2CF_3$ | c-Pen |
| 24 | Me | $CHFCH_2CF_3$ | n-Hex |
| 25 | Me | $CH(CF_3)_2$ | s-Bu |
| 26 | Me | CN | $CHF_2$ |
| 27 | Me | COOMe | $CHF_2$ |
| 28 | Me | COOEt | $CHF_2$ |
| 29 | Me | COO(i-Pr) | $CH_2CN$ |
| 30 | Me | COO(s-Bu) | $CH_2COO(s-Bu)$ |
| 31 | Me | $COOCH(CH_3)CH(CH_3)_2$ | $CHF_2$ |
| 32 | Me | COO(s-Bu) | $CH_2Ph$ |
| 33 | Me | $COOCH(CH_3)CH(CH_3)_2$ | $CH_2Ph$ |
| 34 | Et | $CH_2F$ | $CH_2CH=C(CH_3)_2$ |
| 35 | Et | $CHF_2$ | $CH_2C\equiv CH$ |
| 36 | Et | $CF_3$ | $CH_2C=CCH_2CF_3$ |
| 37 | Et | $CHFCF_3$ | Et |
| 38 | Et | $CF_2CF_3$ | Et |
| 39 | n-Pr | $CHFCH_2CF_3$ | n-Pr |
| 40 | n-Pr | $CH(CF_3)_2$ | $CH_2CH_2CHClCH_3$ |
| 41 | n-Pr | CN | $CH(CH_3)CH_2CF_3$ |
| 42 | n-Pr | COOMe | $CH=CH_2$ |
| 43 | i-Pr | COOEt | $CH_2CO_2Et$ |
| 44 | i-Pr | COO(i-Pr) | $CH_2CO_2(i-Pr)$ |
| 45 | i-Pr | COO(s-Bu) | $CH_2C\equiv CH$ |
| 46 | i-Pr | $CO_2CH(CH_3)CH(CH_3)_2$ | $CH_2C=CCH_2CF_3$ |
| 47 | Ph | $CHF_2$ | $CH_2Ph$ |
| 48 | Ph | $CF_3$ | $CHF_2$ |
| 49 | Ph | $CHFCF_3$ | $CH=CH_2$ |
| 50 | Ph | $CF_2CF_3$ | $CH_2C\equiv CH$ |

EXAMPLES

Next, the process for production of the present compound is specifically described by way of Examples. However, the present invention is in no way restricted by these Examples.

Reference Example 1

Synthesis of 5-hydroxy-1-methyl-3-trifluoromethylpyrazole 92.1 g (0.5 mole) of ethyl 4,4,4-trifluoroacetoacetate was dissolved in 60.1 g (1.0 mole) of acetic acid. The solution was cooled to 10° C. or lower with stirring. Thereto was dropwise added, in 1 hour, 65.8 g (0.5 mole) of a 35% aqueous methylhydrazine solution. After the dropwise addition, the mixture was stirred at room temperature for 1 hour and successively at 80° C. for 5 hours to give rise to a reaction. After the reaction, the mixture was cooled to room temperature. Thereto were added 150 ml of toluene, 600 ml of water and 48 g (1.2 moles) of sodium hydroxide. After phase separation, 154 g (1.5 moles) of 35% hydrochloric acid was added to the aqueous layer. The resulting crystals were collected by filtration, washed with 50 ml of water twice, and dried in a hot-air drier, to obtain 71.8 g (yield: 86.5%) of a title compound as light yellow crystals.

LC-MS (EI): m/z=166 ($M^+$)
Melting point: 179-180° C.

Reference Example 2

Synthesis of 5-hydroxy-1-phenyl-3-trifluoromethylpyrazole 18.4 g (0.1 mole) of ethyl 4,4,4-trifluoroacetoacetate was dissolved in 12.0 g (0.2 mole) of acetic acid. The solution was cooled to 10° C. or lower with stirring. Thereto was dropwise added, in 0.5 hour, 11.8 g (0.11 mole) of phenylhydrazine. After the dropwise addition, the mixture was stirred at room temperature for 1 hour and successively at 80° C. for 5 hours to give rise to a reaction. After the reaction, the mixture was cooled to room temperature. Thereto were added 100 ml of water. The resulting crystals were collected by filtration, washed with 50 ml of water twice, and dried in a hot-air drier, to obtain 22.3 g (yield: 98.0%) of a title compound as light yellow crystals.

LC-MS (EI): m/z=228 ($M^+$)
Melting point: 190-192° C.

Reference Example 3

Synthesis of 3-ethoxycarbonyl-5-hydroxy-1-methylpyrazole 50.0 g (0.24 mole) of diethyl oxaloacetate sodium salt was suspended in 500 ml of ethanol. Thereto was added 25 ml of acetic acid. Thereto was dropwise added, at room temperature in 0.5 hour with stirring, 15 g (0.33 mole) of 97% methylhydrazine. After the dropwise addition, the mixture was stirred at room temperature for 2 hours and successively at the refluxing temperature for 5 hours. After cooling, ethanol was distilled off under reduced pressure. To the residue were added 200 ml of ethyl acetate and 100 ml of water. After phase separation, the aqueous layer was subjected to re-extraction with 50 ml of ethyl acetate. The two ethyl acetate layers were combined and washed with 50 ml of water and 50 ml of a saturated aqueous sodium chloride 50 ml of a saturated aqueous sodium chloride solution in this order. The resulting ethyl acetate layer was dried over anhydrous sodium sulfate and subjected to vacuum distillation to remove the solvent. To the resulting crystals was added 100 ml of water. The crystals were collected by filtration, washed with 10 ml of water, and dried in a hot-air drier, to obtain 29.2 g (yield: 71.8%) of a title compound as light yellow crystals.

LC-MS (EI): m/z=170 ($M^+$), 125 (base)
Melting point: 151° C.

Reference Example 4

Synthesis of 3-cyano-5-hydroxy-1-phenylpyrazole 120 ml of water and 15 ml of 35% hydrochloric acid were added to 5.6 g (0.06 mole) of aniline to obtain a solution. The solution was ice-cooled to 0 to 5° C. Thereto was drop-wise added, with stirring, 24 ml of water in which 4.2 g (0.06 mole) of sodium nitrite had been dissolved, after which stirring was conducted for 1 hour. Then, this aqueous diazonium salt solution was dropwise added to 120 ml of a pyridine solution containing 10.2 g (0.06 mole) of diethyl α-cyanosuccinate, with stirring under ice-cooling. After the dropwise addition, the mixture was stirred for 1 hour under ice-cooling and successively for 1 hour at room temperature, to give rise to a reaction. After the reaction, 240 ml of a 2% aqueous sodium hydroxide solution was added, followed by stirring for 2 hours. Then, the reaction mixture was drop-wise added to 240 ml of 35% hydrochloric acid under ice-cooling. The resulting crystals were collected by filtration, washed with 10 ml of water, and dried in a hot-air drier, to obtain 8.4 g of crude, reddish brown crystals of title compound. The crude crystals were recrystallized from diethyl ether-petroleum ether and dried in a hot-air drier, to obtain 5.7 g (yield: 51.3%) of a title compound as light yellow crystals.

LC-MS (EI): m/z=185 ($M^+$), 125 (base)
Melting point: 190° C.

Example 1

Synthesis of 5-difluoromethoxy-4-hydroxymethyl-1-methyl-3-trifluoromethylpyrazole 16.6 g (0.10 mole) of the 5-hydroxy-1-methyl-3-trifluoromethylpyrazole synthesized in Reference Example 1 was dissolved in 35.0 g (0.15 mole) of a 24% aqueous potassium hydroxide solution. To the solution being stirred at room temperature was dropwise added 9.7 g (0.12 mole) of a 37% formalin solution, followed by stirring at the same temperature for 1 hour. Then, there were added 70.0 g (0.3 mole) of a 24% aqueous potassium hydroxide solution and 100 ml of acetonitrile. Therein was blown 17.3 g (0.20 mole) of chlorodifluoromethane at room temperature in 2 hours, followed by stirring at room temperature for 2 hours to give rise to a reaction. After the reaction, the organic layer which appeared by phase separation, was concentrated under reduced pressure to obtain 26.5 g (purity: 82.0%, yield: 88.2%) of a crude solution of title compound. The crude solution was subjected to vacuum distillation to obtain a title compound as a colorless transparent solution.

$^1$H-NMR (300 MHz, DMSO-$d_6$): δ
7.23 (t, J=72 Hz, 1H), 5.29 (t, J=5.1 Hz, 1H),
4.36 (d, J=5.1 Hz, 2H), 3.77 (s, 3H) ppm
GC-MS (EI): m/z=246 ($M^+$), 177 (base)
Boiling point: 103-105° C./0.53 kPa

Example 2

Synthesis of 4-hydroxymethyl-5-methoxy-1-methyl-3-trifluoromethylpyrazole

In 100 ml of DMF were suspended 16.6 g (0.10 mole) of the 5-hydroxy-1-methyl-3-trifluoromethylpyrazole synthesized in Reference Example 1 and 20.9 g (0.15 mole) of potassium carbonate. In this suspension being stirred at room temperature was placed 4.5 g (0.15 mole) of paraformaldehyde, followed by stirring at the same temperature for 1 hour. Then, 41.8 g (0.30 mole) of potassium carbonate was added. Thereto was dropwise added 42.6 g (0.30 mole) of methyl iodide, followed by stirring at room temperature for 2 hours to give rise to a reaction. After the reaction, 200 ml of ethyl acetate and 200 ml of water were added. The organic layer, which appeared by phase separation, was separated. The aqueous layer was subjected to re-extraction with 50 ml of ethyl acetate. The two organic layers were combined and washed with 50 ml of water, 30 ml of a saturated aqueous ammonium chloride solution and 30 ml of a saturated aqueous sodium chloride solution in this order. The resulting organic layer was dried over anhydrous sodium sulfate and then concentrated under reduced pressure to obtain 24.9 g (purity: 67.5%, yield: 79.0%) of a crude solution of title compound. The crude solution was subjected to vacuum distillation to obtain a title compound as a light yellow transparent solution.

$^1$H-NMR (300 MHz, CDCl$_3$): δ
4.60 (s, 2H), 4.13 (s, 3H), 3.69 (s, 3H), 2.02 (br, 1H) ppm
GC-MS (EI) m/z=210 (M$^+$), 193 (base)
Boiling point: 80-82° C./26.7 Pa

Example 3

Synthesis of 4-hydroxymethyl-5-methoxy-1-methyl-3-trifluoromethylpyrazole

In 100 ml of DMF were suspended 16.6 g (0.10 mole) of the 5-hydroxy-1-methyl-3-trifluoromethylpyrazole synthesized in Reference Example 1 and 20.9 g (0.15 mole) of potassium carbonate. In this suspension being stirred at room temperature was placed 4.5 g (0.15 mole) of paraformaldehyde, followed by stirring at the same temperature for 1 hour. Then, 41.8 g (0.30 mole) of potassium carbonate was added. Thereto was dropwise added 25.2 g (0.20 mole) of dimethyl sulfate, followed by stirring at room temperature for 2 hours to give rise to a reaction. After the reaction, 200 ml of ethyl acetate and 200 ml of water were added. The organic layer, which appeared by phase separation, was separated. The aqueous layer was subjected to re-extraction with 50 ml of ethyl acetate. The two organic layers were combined and washed with 50 ml of water, 30 ml of a saturated aqueous ammonium chloride solution and 30 ml of a saturated aqueous sodium chloride solution in this order. The resulting organic layer was dried over anhydrous sodium sulfate and then concentrated under reduced pressure to obtain 23.5 g (purity: 75.4%, yield: 84.3%) of a crude solution of title compound. The crude solution was subjected to vacuum distillation to obtain a title compound. The compound showed spectra identical to those indicated in Example 2.

Example 4

Synthesis of 5-ethoxy-4-hydroxymethyl-1-methyl-3-trifluoromethylpyrazole

In 100 ml of DMF were suspended 16.6 g (0.10 mole) of the 5-hydroxy-1-methyl-3-trifluoromethylpyrazole synthesized in Reference Example 1 and 20.9 g (0.15 mole) of potassium carbonate. In this suspension being stirred at room temperature was placed 4.5 g (0.15 mole) of paraformaldehyde, followed by stirring at the same temperature for 1 hour. Then, 41.8 g (0.30 mole) of potassium carbonate was added. Thereto was dropwise added 21.8 g (0.20 mole) of bromoethane. The reaction mixture was heated to 60° C. and stirred for 8 hours to give rise to a reaction. After the reaction, 200 ml of ethyl acetate and 200 ml of water were added. The organic layer, which appeared by phase separation, was separated. The aqueous layer was subjected to re-extraction with 50 ml of ethyl acetate. The two organic layers were combined and washed with 50 ml of water, 30 ml of a saturated aqueous ammonium chloride solution and 30 ml of a saturated aqueous sodium chloride solution in this order. The resulting organic layer was dried over anhydrous sodium sulfate and then concentrated under reduced pressure to obtain 22.5 g (purity: 82.7%, yield: 83.0%) of a crude solution of title compound. The crude solution was subjected to vacuum distillation to obtain a title compound as a colorless transparent solution.

$^1$H-NMR (300 MHz, CDCl$_3$): δ
4.57 (s, 2H), 4.36 (q, J=7.2 Hz, 2H), 3.71 (s, 3H),
1.73 (br, 1H), 1.43 (t, J=7.2 Hz, 3H) ppm
GC-MS (EI) m/z=224 (M$^+$), 177 (base)
Boiling point: 95-97° C./26.7 Pa

Example 5

Synthesis of 4-hydroxymethyl-5-isopropyloxy-1-methyl-3-trifluoromethylpyrazole In 100 ml of DMF were suspended 16.6 g (0.10 mole) of the 5-hydroxy-1-methyl-3-trifluoromethylpyrazole synthesized in Reference Example 1 and 20.9 g (0.15 mole) of potassium carbonate. In this suspension being stirred at room temperature was placed 4.5 g (0.15 mole) of paraformaldehyde, followed by stirring at the same temperature for 1 hour. Then, 41.8 g (0.30 mole) of potassium carbonate was added. Thereto was dropwise added 36.9 g (0.30 mole) of isopropyl bromide. The reaction mixture was heated to 60° C. and stirred for 12 hours to give rise to a reaction. After the reaction, 200 ml of ethyl acetate and 200 ml of water were added. The organic layer, which appeared by phase separation, was separated. The aqueous layer was subjected to re-extraction with 50 ml of ethyl acetate. The two organic layers were combined and washed with 50 ml of water, 30 ml of a saturated aqueous ammonium chloride solution and 30 ml of a saturated aqueous sodium chloride solution in this order. The resulting organic layer was dried over anhydrous sodium sulfate and then concentrated under reduced pressure to obtain 21.7 g (purity: 59.4%, yield: 53.5%) of a crude solution of title compound. The crude solution was subjected to vacuum distillation to obtain a title compound as a light yellow transparent solution.

$^1$H-NMR (300 MHz, CDCl$_3$): δ
4.7-4.6 (m, 1H), 4.53 (s, 2H), 3.71 (s, 3H),
1.85 (br, 1H), 1.38 (d, J=6.3 Hz, 6H) ppm
GC-MS (EI) m/z=231 (M$^+$), 178 (base)
Boiling point: 106-107° C./106.7 Pa

Example 6

Synthesis of 5-cyclopentyloxy-4-hydroxymethyl-1-methyl-3-trifluoromethylpyrazole In 100 ml of DMF were suspended 16.6 g (0.10 mole) of the 5-hydroxy-1-methyl-3-trifluoromethylpyrazole synthesized in Reference Example 1 and 20.9 g (0.15 mole) of potassium carbonate. In this suspension being stirred at room temperature was placed 4.5 g (0.15 mole) of paraformaldehyde, followed by stirring at the same temperature for 1 hour. Then, 41.8 g (0.30 mole) of potassium carbonate was added. Thereto was dropwise added 44.7 g (0.30 mole) of cyclopentyl bromide. The reaction mixture was heated to 60° C., followed by stirring for 12 hours to give rise to a reaction. After the reaction, 200 ml of ethyl acetate and 200 ml of water were added. The organic layer, which appeared by phase separation, was separated. The aqueous layer was subjected to re-extraction with 50 ml of ethyl acetate. The two organic layers were combined and washed with 50 ml of water, 30 ml of a saturated aqueous ammonium chloride solution and 30 ml of a saturated aqueous sodium chloride solution in this order. The resulting organic layer was dried over anhydrous sodium sulfate and then concentrated under reduced pressure to obtain 41.9 g (purity: 42.2%, yield: 67.0%) of a crude solution of title compound. The crude solution was subjected to vacuum distillation to obtain a title compound as a light yellow transparent solution.

$^1$H-NMR (300 MHz, CDCl$_3$): δ
5.0-5.1 (m, 1H), 4.56 (s, 2H), 3.68 (s, 3H),
2.19 (s, 1H), 1.9-1.6 (m, 8H) ppm
GC-MS (EI): m/z=264 (M$^+$), 178 (base)
Boiling point: 105-107° C./26.7 Pa

Example 7

Synthesis of 5-benzyloxy-4-hydroxymethyl-1-methyl-3-trifluoromethylpyrazole 16.6 g (0.10 mole) of the 5-hydroxy-1-methyl-3-trifluoromethylpyrazole synthesized in Reference Example 1 was dissolved in 35.0 g (0.15 mole) of a 24% aqueous potassium hydroxide solution. To the solution being stirred at room temperature was dropwise added 9.7 g (0.12 mole) of a 37% formalin solution, followed by stirring at the same temperature for 1 hour. Then, there were added 70.0 g (0.3 mole) of a 24% aqueous potassium hydroxide solution and 100 ml of acetonitrile. Thereto was dropwise added 20.5 g (0.12 mole) of benzyl bromide at room temperature in 1 hour, followed by stirring at room temperature for 12 hours to give rise to a reaction. After the reaction, the organic layer which appeared by phase separation, was concentrated under reduced pressure to obtain 26.1 g (purity: 80.0%, yield: 73.1%) of a crude solution of title compound. The crude solution was purified by silica gel column chromatography (n-hexane:ethyl acetate=5:1) to obtain a title compound as a light yellow transparent solution.

$^1$H-NMR (300 MHz, CDCl$_3$): δ
7.4-7.3 (m, 5H), 5.28 (s, 2H), 4.56 (d, J=5.7 Hz, 2H),
3.51 (s, 3H), 1.74 (t, J=5.7 Hz, 1H) ppm
GC-MS (EI) m/z=286 (M$^+$), 91 (base)

Example 8

Synthesis of 5-ethoxycarbonylmethyloxy-4-hydroxymethyl-1-methyl-3-trifluoromethylpyrazole In 100 ml of DMF were suspended 16.6 g (0.10 mole) of the 5-hydroxy-1-methyl-3-trifluoromethylpyrazole synthesized in Reference Example 1 and 20.9 g (0.15 mole) of potassium carbonate. In this suspension being stirred at room temperature was placed 4.5 g (0.15 mole) of paraformaldehyde, followed by stirring at the same temperature for 1 hour. Then, 41.8 g (0.30 mole) of potassium carbonate was added. Thereto was dropwise added 93.4 g (0.20 mole) of ethyl bromoacetate, followed by stirring at room temperature for 2 hours to give rise to a reaction. After the reaction, 200 ml of ethyl acetate and 200 ml of water were added. The organic layer, which appeared by phase separation, was separated. The aqueous layer was subjected to re-extraction with 50 ml of ethyl acetate. The two organic layers were combined and washed with 50 ml of water, 30 ml of a saturated aqueous ammonium chloride solution and 30 ml of a saturated aqueous sodium chloride solution in this order. The resulting organic layer was dried over anhydrous sodium sulfate and then concentrated under reduced pressure to obtain 44.7 g (purity: 63.0%, yield: 81.9%) of a crude solution of title compound. The crude solution was subjected to vacuum distillation to obtain a light yellow transparent solution. N-Hexane was added to the solution. The resulting white crystals were collected by suction filtration to obtain a title compound as white crystals.

$^1$H-NMR (300 MHz, CDCl$_3$): δ
5.18 (t, J=4.5 Hz, 1H), 5.06 (s, 2H),
4.19 (q, J=7.2 Hz, 2H), 3.75 (s, 3H),
1.22 (t, J=7.2 Hz, 3H) ppm
Boiling point: 142° C./33.3 Pa
Melting point: 57-59° C.

Example 9

Synthesis of 5-propargyloxy-4-hydroxymethyl-1-methyl-3-trifluoromethylpyrazole In 100 ml of DMF were suspended 16.6 g (0.10 mole) of the 5-hydroxy-1-methyl-3-trifluoromethylpyrazole synthesized in Reference Example 1 and 20.9 g (0.15 mole) of potassium carbonate. In this suspension being stirred at room temperature was placed 4.5 g (0.15 mole) of paraformaldehyde, followed by stirring at the same temperature for 1 hour. Then, 41.8 g (0.30 mole) of potassium carbonate was added. Thereto was dropwise added 23.8 g (0.20 mole) of propargyl bromide. The reaction mixture was heated to 60° C. and stirred for 2 hours to give rise to a reaction. After the reaction, 200 ml of ethyl acetate and 200 ml of water were added. The organic layer, which appeared by phase separation, was separated. The aqueous layer was subjected to re-extraction with 50 ml of ethyl acetate. The two organic layers were combined and washed with 50 ml of water, 30 ml of a saturated aqueous ammonium chloride solution and 30 ml of a saturated aqueous sodium chloride solution in this order. The resulting organic layer was dried over anhydrous sodium sulfate and then concentrated under reduced pressure to obtain 31.2 g (purity: 36.9%, yield: 49.2%) of a crude solution of title compound. The crude solution was subjected to vacuum distillation to obtain a title compound as a light yellow transparent solution.

$^1$H-NMR (300 MHz, CDCl$_3$): δ
4.95 (d, J=2.4 Hz, 2H), 4.61 (s, 2H), 3.77 (s, 3H), 2.63 (t, J=2.4 Hz, 1H), 1.78 (s, 1H) ppm
GC-MS (EI) m/z=234 (M⁺), 203 (base)
Boiling point: 99-101° C./133.3 Pa Example 10

Synthesis of 5-difluoromethoxy-4-hydroxymethyl-1-phenyl-3-trifluoromethylpyrazole 22.8 g (0.10 mole) of the 5-hydroxy-1-phenyl-3-trifluoromethylpyrazole synthesized in Reference Example 2 was dissolved in 35.0 g (0.15 mole) of a 24% aqueous potassium hydroxide solution. To the solution being stirred at room temperature was dropwise added 9.7 g (0.12 mole) of a 37% formalin solution, followed by stirring at the same temperature for 1 hour. Then, there were added 70.0 g (0.3 mole) of a 24% aqueous potassium hydroxide solution and 100 ml of acetonitrile. Therein was blown 17.3 g (0.20 mole) of chlorodifluoromethane at room temperature in 2 hours, followed by stirring at room temperature for 2 hours to give rise to a reaction. After the reaction, the organic layer which appeared by phase separation, was concentrated under reduced pressure to obtain 28.0 g (purity: 93.6%, yield: 84.9%) of a crude solution of title compound. The crude solution was purified by silica gel column chromatography (n-hexane:ethyl acetate=5:1) to obtain a title compound as white crystals.
¹H-NMR (300 MHz, CDCl₃): δ
7.6-7.4 (m, 5H), 6.67 (t, J=72 Hz, 1H),
4.68 (d, J=5.7 Hz, 2H), 1.91 (t, J=5.7 Hz, 1H) ppm
GC-MS (EI) m/z=308 (M⁺), 77 (base)
Melting point: 57-59° C.

Example 11

Synthesis of 3-ethoxycarbonyl-5-difluoromethoxy-4-hydroxymethyl-1-methylpyrazole In 50 ml of DMF were suspended 8.5 g (0.05 mole) of the 3-ethoxycarbonyl-5-hydroxy-1-methylpyrazole synthesized in Reference Example 3 and 10.5 g (0.08 mole) of potassium carbonate. In this suspension being stirred at room temperature was placed 2.3 g (0.08 mole) of paraformaldehyde, followed by stirring at the same temperature for 1 hour. Then, 20.9 g (0.15 mole) of potassium carbonate was added. Therein was blown 8.6 g (0.10 mole) of chlorodifluoromethane. The reaction mixture was stirred at room temperature for 2 hours to give rise to a reaction. After the reaction, 200 ml of ethyl acetate and 200 ml of water were added. The organic layer, which appeared by phase separation, was separated. The aqueous layer was subjected to re-extraction with 50 ml of ethyl acetate three times. The organic layers were combined and washed with 50 ml of water, 30 ml of a saturated aqueous ammonium chloride solution and 30 ml of a saturated aqueous sodium chloride solution in this order. The resulting organic layer was dried over anhydrous sodium sulfate and then concentrated under reduced pressure to obtain 24.3 g (purity: 42.2%, yield: 82.0%) of a crude solution of title compound. The crude solution was purified by silica gel column chromatography (n-hexane:ethyl acetate=1:1) to obtain a title compound as white crystals.
¹H-NMR (300 MHz, CDCl₃): δ
6.61 (q, J=71.7 Hz, 1H), 4.62 (d, J=6.9 Hz, 2H),
4.46 (t, J=7.2 Hz, 2H), 3.84 (s, 3H),
3.62 (t, J=6.9 Hz, 1H), 1.43 (t, J=7.2 Hz, 3H) ppm
GC-MS (EI) m/z=250 (M⁺), 153 (base)
Melting point: 90-91° C.

Example 12

Synthesis of 3-cyano-5-difluoromethoxy-4-hydroxymethyl-1-phenylpyrazole 18.5 g (0.10 mole) of the 3-cyano-5-hydroxy-1-phenylpyrazole synthesized in Reference Example 4 was dissolved in 35.0 g (0.15 mole) of a 24% aqueous potassium hydroxide solution. To the solution being stirred at room temperature was dropwise added 9.7 g (0.12 mole) of a 37% formalin solution, followed by stirring at the same temperature for 1 hour. Then, there were added 70.0 g (0.3 mole) of a 24% aqueous potassium hydroxide solution and 100 ml of acetonitrile. Therein was blown 17.3 g (0.20 mole) of chlorodifluoromethane at room temperature in 2 hours, followed by stirring at room temperature for 2 hours to give rise to a reaction. After the reaction, the organic layer which appeared by phase separation, was concentrated under reduced pressure to obtain 24.6 g (purity: 70.6%, yield: 65.5%) of a crude solution of title compound. The crude solution was purified by silica gel column chromatography (n-hexane:ethyl acetate=3:1) to obtain a title compound as white crystals.
¹H-NMR (300 MHz, CDCl₃): δ
7.6-7.4 (m, 5H), 4.72 (d, J=5.1 Hz, 2H),
2.10 (t, J=5.1 Hz, 1H) ppm
GC-MS (EI) m/z=265 (M⁺), 77 (base)
Melting point: 71-72° C.

INDUSTRIAL APPLICABILITY

The present invention provides a novel process for industrially producing a 5-alkoxy-4-hydroxymethylpyrazole compound. According to the present process, a 5-alkoxy-4-hydroxymethylyrazole compound is formed from a pyrazole compound represented by the general formula (1) without using a special reactor or an expensive catalyst or transition metal, in a single step in a simple operation under mild conditions at a good yield. Moreover, the present process generates no harmful waste derived from catalyst or transition metal and has a high industrial value.

The invention claimed is:
1. A 5-alkoxy-4-hydroxymethylpyrazole compound represented by formula (4):

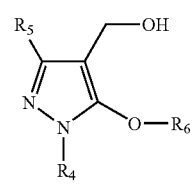

(4)

wherein $R_4$ is a C1 to C6 alkyl group, an aryl group which may have a substituent or a hetero-aryl group which may have a substituent, $R_5$ is a C1 to C6 haloalkyl group, a cyano group or a (C1 to C6 alkoxy)carbonyl group, and $R_6$ is a C1 to C6 alkyl group which is unsubstituted or substituted with halogen, phenyl group, cyano group or (C1 to C6 alkoxy)carbonyl group, a C3 to C8 cycloalkyl group which is unsubstituted or substituted with halogen, phenyl group, cyano group or (C1 to C6 alkoxy) carbonyl group, a C2 to C6 alkenyl group which is unsubstituted or substituted with halogen, phenyl group, cyano group or (C1 to C6 alkoxy)carbonyl group, or a C2 to C6 alkynyl group which is unsubstituted or substituted with halogen, phenyl group, cyano group or (C1 to C6 alkoxy)carbonyl group.

2. The 5-alkoxy-4-hydroxymethylpyrazole compound according to claim 1, wherein $R_5$ is a (mono-, di- or tri-fluoro) methyl group.

3. The 5-alkoxy-4-hydroxymethylpyrazole compound according to claim 1, wherein $R_5$ is a trifluoromethyl group.

4. The 5-alkoxy-4-hydroxymethylpyrazole compound according to claim 1, wherein $R_5$ is a cyano group.

5. The 5-alkoxy-4-hydroxymethylpyrazole compound according to claim 1, wherein $R_5$ is a (C1 to C6 alkoxy)carbonyl group.

6. The 5-alkoxy-4-hydroxymethylpyrazole compound according to claim 1, wherein $R_5$ is an ethoxycarbonyl group.

7. The 5-alkoxy-4-hydroxymethylpyrazole compound according to claim 1, wherein $R_4$ is a methyl group, $R_5$ is a trifluoromethyl group, and $R_6$ is a (mono-, di- or tri-halogen substituted)methyl group.

8. The 5-alkoxy-4-hydroxymethylpyrazole compound according to claim 1, wherein $R_4$ is a methyl group, $R_5$ is a trifluoromethyl group, and $R_6$ is a difluoromethyl group.

9. A process for producing a 5-alkoxy-4-hydroxymethylpyrazole compound of formula (4) of claim 1, the process comprising:

reacting a pyrazole compound represented by formula (1):

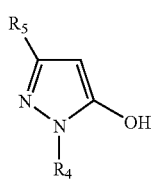

(1)

with a compound represented by formula (2):

L-$R_6$ (2)

(wherein L is a leaving group and $R_4$ and $R_5$ are as defined in claim 1) in the presence of a base and formaldehyde.

10. The process for producing a 5-alkoxy-4-hydroxymethylpyrazole compound according to claim 9, wherein the leaving group represented by L is a halogen atom, an alkylsulfonyloxy group, a haloalkylsulfonyloxy group, or a benzenesulfonyloxy group which may have a substituent.

11. The process for producing a 5-alkoxy-4-hydroxymethylpyrazole compound according to claim 10, wherein $R_5$ is a (mono-, di- or tri- fluoro) methyl group.

12. The process for producing a 5-alkoxy-4-hydroxymethylpyrazole compound according to claim 10, wherein $R_5$ is a trifluoromethyl group.

13. The process for producing a 5-alkoxy-4-hydroxymethylpyrazole compound according to claim 10, wherein $R_5$ is a cyano group.

14. The process for producing a 5-alkoxy-4-hydroxymethylpyrazole compound according to claim 10, wherein $R_5$ is a (C1 to C6 alkoxy)carbonyl group.

15. The process for producing a 5-alkoxy-4-hydroxymethylpyrazole compound according to claim 10, wherein withdrawing group represented by $R_5$ is an ethoxycarbonyl group.

16. The process for producing a 5-alkoxy-4-hydroxymethylpyrazole compound according to claim 10, wherein the leaving group represented by L is a halogen atom.

17. The process for producing a 5-alkoxy-4-hydroxymethylpyrazole compound according to claim 10, wherein the leaving group represented by L is a chlorine atom and $R_6$ is a difluoromethyl group.

18. The process for producing a 5-alkoxy-4-hydroxymethylpyrazole compound according to claim 9, wherein $R_4$ is a methyl group, $R_5$ is a trifluoromethyl group, and the compound represented by formula (2) is a chloro(mono-, di- or tri-halogen substituted) methane.

19. The process for producing a 5-alkoxy-4-hydroxymethylpyrazole compound according to claim 9, wherein $R_4$ is a methyl group, $R_5$ is a trifluoromethyl group, and the compound represented by formula (2) is chlorodifluoromethane.

20. The process for producing a 5-alkoxy-4-hydroxymethylpyrazole compound according to claim 9, wherein $R_5$ is a (mono-, di- or tri-fluoro) methyl group.

21. The process for producing a 5-alkoxy-4-hydroxymethylpyrazole compound according to claim 9, wherein $R_5$ is a trifluoromethyl group.

22. The process for producing a 5-alkoxy-4-hydroxymethylpyrazole compound according to claim 9 wherein $R_5$ is a cyano group.

23. The process for producing a 5-alkoxy-4-hydroxymethylpyrazole compound according to claim 9, wherein $R_5$ is a (C1 to C6 alkoxy)carbonyl group.

24. The process for producing a 5-alkoxy-4-hydroxymethylpyrazole compound according to claim 9, wherein $R_5$ is an ethoxycarbonyl group.

* * * * *

UNITED STATES PATENT AND TRADEMARK OFFICE
CERTIFICATE OF CORRECTION

| | | |
|---|---|---|
| PATENT NO. | : 7,812,175 B2 | Page 1 of 1 |
| APPLICATION NO. | : 12/223123 | |
| DATED | : October 12, 2010 | |
| INVENTOR(S) | : Yukio Uchida et al. | |

It is certified that error appears in the above-identified patent and that said Letters Patent is hereby corrected as shown below:

Column 24, lines 14-15, (claim 15, lines 2 and 3) delete "withdrawing group represented by".

Signed and Sealed this

Eighteenth Day of September, 2012

David J. Kappos
*Director of the United States Patent and Trademark Office*